United States Patent [19]

MacLaury

[11] 4,192,957
[45] Mar. 11, 1980

[54] DEHYDROHALOGENATION OF A DIPHENYL TRICHLOROETHANE

[75] Inventor: Michael R. MacLaury, Rexford, N.Y.

[73] Assignee: General Electric Company, Schenectady, N.Y.

[21] Appl. No.: 11,104

[22] Filed: Feb. 12, 1979

[51] Int. Cl.² ............................................. C07C 37/00
[52] U.S. Cl. .................................................... 568/726
[58] Field of Search ......................................... 568/726

[56] References Cited

U.S. PATENT DOCUMENTS

| | | | |
|---|---|---|---|
| 4,097,538 | 6/1978 | Factor et al. | 568/726 |
| 4,117,018 | 9/1978 | Cleveland et al. | 568/726 |

*Primary Examiner*—Norman Morgenstern
*Attorney, Agent, or Firm*—Joseph T. Cohen; Leo I. MaLossi

[57] ABSTRACT

The action of liquid ammonia in dehydrohalogenating 1,1,1-trichloro-2,2-bis(4-hydroxyphenyl)ethane to 1,1-dichloro-2,2-bis(4-hydroxyphenyl)ethylene by liquid ammonia can be accelerated by incorporating in the liquid ammonia an effective amount of a certain class of alkyl amine hydrohalides.

7 Claims, No Drawings

DEHYDROHALOGENATION OF A DIPHENYL TRICHLOROETHANE

This invention is concerned with a process for dehydrohalogenating a dihydroxy diphenyl trichloroethane. More particularly, the invention is concerned with a process for obtaining in good yield, high purity and at an increased rate of reaction the compound 1,1-dichloro-2,2-bis(4-hydroxyphenyl)ethylene (hereinafter referred to as "dichloride") having the formula

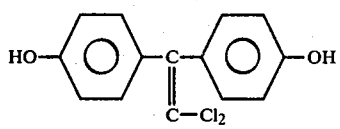

by treating 1,1,1-trichloro-2,2-bis(4-hydroxyphenyl)ethane (hereinafter referred to as "trichloride") having the formula

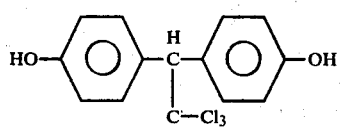

with anhydrous liquid ammonia in an amount sufficient to act as both dehydrohalogenating agent and solvent, the said liquid ammonia containing an amount of certain alkyl amine hydrohalides (hereinafter designated as "alkyl amine") effective to accelerate the dehydrohalogenation reaction, wherein said alkyl amine is selected from the class consisting of methylamine hydrochloride and bromide, ethylamine hydrochloride and bromide, and dimethylamine hydrochloride and bromide, thereby to form a substantially pure dichloride of the above formula I, and removing the unreacted ammonia and alkyl amine, and isolating the desired dichloride.

U.S. Pat. No. 4,097,538—Factor et al, issued June 27, 1978 and assigned to the same assignee as the present invention, discloses the dehydrohalogenation of the compound of formula II with liquid ammonia wherein the latter is acting as both a dehydrohalogenating agent and as a solvent. As pointed out in that patent, this process produces the dichloride in high yield and of high purity. However, it has been found that the rate of dehydrohalogenation in the liquid ammonia is not as rapid as would be desired, and for optimum commercial utilization of this dehydrohalogenation process, it would be an important advantage to accelerate the rate of dehydrohalogenation.

In U.S. patent application Ser. No. 4050 filed Jan. 17, 1979 (RD-10820—MacLaury), and assigned to the same assignee as the present invention, is disclosed a process for dehydrohalogenating the above-identified trichloride to form the dichloride by using liquid methylamine as the dehydrohalogenating agent. As pointed out in this patent application, the liquid methylamine greatly accelerates the reaction whereby the dehydrochlorination takes place, although with sacrifice in the purity of the final dichloride.

It is accordingly one of the objects of the invention to effect dehydrohalogenation of the trichloride to the dichloride rapidly without sacrifice in the purity and yield of the dichloride.

It is a still further object of the invention to effect dehydrochlorination of the aforesaid trichloride using liquid ammonia as the dehydrohalogenating agent and yet be able to accelerate the dehydrohalogenating effect of the liquid ammonia, while at the same time maintaining the high purity and yield which accompany the use of the liquid ammonia alone.

Other objects of the invention will become more apparent from the discussion which follows.

In accordance with my invention, I have unexpectedly discovered that small amounts of alkyl amine hydrohalides of the class described above when added to liquid ammonia used as the dehydrohalogenating agent significantly increase the rate of dehydrohalogenation while retaining the advantages of the liquid ammonia in obtaining a high purity material in good yield. The purified dichloride thus obtained, after isolation needs little if any purification and can be used to make flame-resistant and flame-retardant resins by treatment of the dichloride of formula I with either diphenyl carbonate or phosgene to form polycarbonate resins.

It was entirely unexpected and in no way could have been predicted that the aforementioned class of alkyl amines would be able to accelerate the dehydrohalogenating action of the liquid ammonia. For example, under essentially equivalent conditions, it was found that other alkyl amines and alkyl amine hydrochlorides similar to the above-identified class, for instance, diethyl amine, diethyl amine hydrochloride, and triethyl amine hydrochloride, either reduced the rate of reaction or contributed little if anything to accelerating the rate of dehydrohalogenation. What was even more unexpected was to find that even though, as pointed out above, methylamine by itself greatly increased the dehydrohalogenation of the trichloride, when an amount of methylamine equivalent to methylamine hydrochloride that I had found effective was used with the liquid ammonia, essentially no accelerating effect was noted (a half-life of 48 minutes versus 53 minutes).

It was also unexpectedly discovered that the effect of the alkyl amine on the ammonia was synergistic rather than what might be expected knowing that liquid methylamine alone as a dehydrohalogenating agent operated more rapidly in the dehydrohalogenation step than liquid ammonia alone. Thus, under somewhat similar conditions as in Example 1, if one employed pure methylamine instead of pure ammonia as the dehydrohalogenating agent and solvent medium as described in the aforementioned patent application, Ser. No. 4050, the half-life reaction was about 12.2 minutes accompanied by an increase in impurities which have been discussed above. Table I, which appears in Example 1, illustrates quite clearly the synergistic effect when the tests in connection with methylamine hydrochloride are examined. Thus, referring to Table I, the incorporation of 0.25 mol percent of the methylamine hydrochloride (based on the ammonia) reduced the half-life of the reaction from 53 to 46 minutes, and this half-life was further reduced when as little as 1.12 mol percent methylamine hydrochloride was used. At this point, it is apparent that the advantage of using methylamine hydrochloride is beginning to diminish since when more than double the amount of methylamine hydrochloride (2.52 mol percent) was used, the half-life only dropped to 36 minutes, still a considerable advantage over that achieved using the liquid ammonia alone.

The presence of the small amounts of the alkyl amine with the liquid ammonia does not interfere with the advantages inherent in the use of the ammonia itself. In the first place, no additional solvent of any kind is required since the ammonia acts as both the reactant and the solvent medium. In order to separate the dichloride from the reaction solution, one only needs to allow the ammonia to evaporate from the reactor and remove any alkyl amine by suitable means. Moreover, the dichloride obtained by this procedure after the by-product ammonium chloride and other materials are removed advantageously using a methanol-water medium or water washes, is free of usual impurities in products obtained by previous procedures at a similar stage of purification, for instance, by treating the trichloride with a large molar excess of aqueous sodium hydroxide at elevated temperatures [see M. Trojna and H. Hubacek, Chem. Listy 51, 752 (1957)]. If further purification of the dichloride by crystallization from methanol-water (whose pH has been adjusted to between 3 to 7) is used, the product obtained is as good if not better both in color and in freedom from impurities than products obtained by prior art procedures. Although a large molar excess of ammonia is used to serve both as the reactant and the solvent medium, the dehydrochlorination only uses 1 mol of the ammonia per mol of trichloride, and at the end of the reaction the unused ammonia can be easily recovered by evaporation or distillation. Generally, on a molar ratio from 2 to 20 mols of ammonia are used per mol of the trichloride.

The amount of the alkyl amine used in combination with liquid ammonia can be varied widely and only requires an amount of the former effective to induce the accelerated dehydrohalogenation action of the liquid ammonia. Based on the liquid ammonia employed, one can use from 0.5 to 20%, by weight, or more of the alkyl amine based on the weight of the ammonia. Stated alternatively, the alkyl amine can be used in amounts ranging from about 0.1 to 10 or more mol percent of the alkyl amine based on the molar concentration of the liquid ammonia.

In accordance with my invention, the dehydrochlorination of the trichloride can be achieved by charging the trichloride to a pressure reactor together with the liquid ammonia and the alkyl amine hydrohalide, and thereafter heating the pressure reactor at temperatures ranging from 35° to 125° C. and preferably from 50° to 100° C., for times ranging from about 30 minutes to 6 hours or more to effect dehydrohalogenation. Thereafter, the formed dichloride can be removed from the liquid ammonia-alkyl amine mixture and the ammonium chloride formed, by first allowing the ammonia to volatilize and collecting the latter, and then dissolving the remaining solid material in aqueous methanol and crystallizing the dichloride from that solution by adding water in which the dichloride is insoluble. If further purification is desired, the dichloride can be recrystallized in the manner described above with a methanol-water mixture. It is evident that the size of the pressure reactor used will in many instances dictate the molar concentrations of the ammonia, the alkyl amine, and the trichloride undergoing dehydrohalogenation.

Depending on the temperatures and the amount of ammonia and alkyl amine present in the reactor, pressures ranging from 50 psi to 700–800 psi or more can be employed without materially affecting the results. Again, the temperatures used will depend on the type and size of the pressure reactor employed, the molar concentrations of the ammonia, alkyl amine, the trichloride, etc. Because the reaction using the alkyl amine with the ammonia can be run at somewhat lower temperatures than when ammonia is used alone without any significant increase in impurities, total reaction times of shorter duration are possible than with other methods for dehydrohalogenation. Thus, it has been found that at any reasonable temperature of reaction (50° to 100° C.) the combination of the ammonia and the alkyl amine will cause completion of the dehydrohalogenation reaction in a significantly shorter time than when the ammonia is used alone.

Under the pressure conditions employed in the practice of my invention, temperature, of course is an important function in the attainment of a substantially pure dichloride. Thus, as one proceeds from around room temperature (about 20°–30° C.) to about 125° C., one will find that with the use of reasonable times of reaction, for instance, about 30–90 minutes at the upper end of the temperature range, essentially all of the trichloride is converted to the dichloride in a substantially pure state.

Although the reaction between the ammonia and the trichloride can be carried out without any additional ingredients, the use of aprotic solvents is not precluded. Included among such solvents may be mentioned dimethyl formamide, N-methyl pyrrolidone, N,N-dimethylacetamide, dimethyl sulfoxide, etc. Amounts of such solvents, for instance, by weight, from about 0.1 to 2 parts of the solvent per part of the trichloride, can be used to advantage in some instances in order to reduce the amount of excess liquid ammonia which may be required.

In order that those skilled in the art may better understand how the present invention may be practiced, the following examples are given by way of illustration and not by way of limitation. In some instances, the amounts of ingredients used in the reaction are recited both on a weight and mol percent basis.

EXAMPLE 1

About 20 ml (13 grams, 0.765 mol) ammonia was condensed at −78° C. in a pressure reactor containing 0.6 gram (0.00189 mol) of the trichloride and the specified alkyl amine or alkyl amine hydrochloride. The amine hydrochlorides used in this example were prepared by the reaction of the corresponding amine and gaseous HCl in anhydrous ether. After the ammonia had been condensed, the pressure reactor was sealed and warmed to 50° C., at which point the pressure rose to about 220 psi. The reaction was then allowed to proceed while stirring was conducted in the reaction vessel for a period of about 60 minutes. The reaction mixture was then quenched by cooling the reaction vessel to −78° C., the reaction vessel opened, the ammonia and volatile alkyl amine (if present) allowed to evaporate by applying a vacuum, and the solid material removed by filtration. The balance of the reaction product was analyzed by gas chromatography (130° to 300° C. at 20° C./min. on 3% OV-17) after silylation of the formed dichloride using bis-(trimethylsilyl)-acetamide in the manner described by Klebe et al in J.A.C.S. 38, 3390 (1966). The following Table I shows the results of using various alkyl amines and alkyl amine hydrochlorides with the liquid ammonia in varying concentrations. The heading in the table $T_{\frac{1}{2}}$ (minutes) is indicative of the half-life of the reaction and of the rate of the dehydrohalogenation; the smaller the figure for the $T_{\frac{1}{2}}$, the faster the rate of reaction. When alkyl amines of my invention were used, the level of impurities such as compounds of the formulas

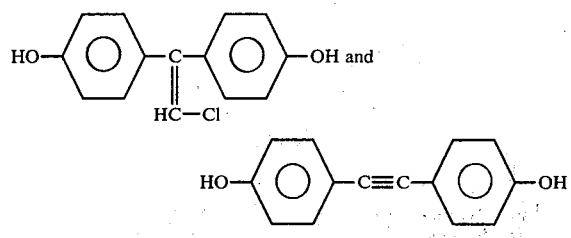

is as low as when the dehydrohalogenation is carried out with the ammonia alone.

TABLE I

| Additive | aWt % | aMol % | b% Tri-chloride | T½(min.) |
|---|---|---|---|---|
| None | — | — | 45.6 | 53 |
| CH3NH2 | 4.54 | 2.47 | 42.2 | 48 |
| CH3NH2 . HCl | 1.00 | 0.25 | 40.6 | 46 |
| CH3NH2 . HCl | 4.46 | 1.12 | 33.6 | 38 |
| CH3NH2 . HCl | 10.00 | 2.52 | 31.9 | 36 |
| (CH3CH2)2NH | 10.62 | 2.47 | 61.4 | 86 |
| (CH3CH2)2NH . HCl | 15.69 | 2.43 | 48.9 | 58 |
| Ch3CH2NH2 . HCl | 11.92 | 2.48 | 29.8 | 35 |
| (CH3)2NH . HCl | 11.92 | 2.48 | 37.4 | 42 |
| (CH3)3N . HCl | 13.84 | 2.46 | 43.5 | 51 | aBased on NH3
bMol % after 60 minutes at 50° C.

EXAMPLE 2

When the amine hydrochlorides described in Example 1 are substituted by corresponding amine hydrobromides, for instance, CH3NH2.HBr, CH3CH2NH2.HBr, and (CH3)2NH.HBr, under the same conditions of reaction, it will be found that the half-life of dehydrohalogenating the trichloride with ammonia will be significantly reduced as compared to the half-life obtained using liquid ammonia free of any such hydrohalides in the dehydrohalogenation reaction.

It will be noted from the above that whereas liquid ammonia without any additive had a half-life of 53 minutes, the incorporation of methylamine hydrochloride even in small amounts such as 1%, by weight, (0.25 mol %) based on the weight of the ammonia, significantly reduced the half-life, and after only moderate increases in the amount of the methylamine hydrochloride, the half-life decreased considerably. It should also be recognized that the compound diethylamine greatly increased the half-life of the reaction (to 86 minutes) and the hydrochloride of this amine, although it did not have as large a half-life, was still in excess of the half-life of the reaction using liquid ammonia without any additive.

The use of small amounts of the alkyl amine hydrochloride in combination with the liquid ammonia will allow the use of lower temperatures and lower pressures and still achieve rapid reaction times. Thus, since the rate at 50° C. is more than doubled by the addition of as low as 1.5 mol percent methyl amine hydrochloride to ammonia (10:1 mol ratio methylamine hydrochloride to trichloride), one could decrease the temperature by at least 10° and have the same reaction rate as obtained with pure ammonia at 50° C. The requirements of very high pressure equipment to contain the ammonia can now be decreased because lower temperatures can be used to achieve the same rates. The ability to use the alkyl amine and particularly the methylamine hydrochloride in small quantities with the liquid ammonia during the dehydrohalogenation reaction will suppress side reactions and undesirable by-products as compared to when liquid methylamine is used alone instead of liquid ammonia.

The dichloride obtained in accordance with the present invention has many uses. One of the more important uses to which this composition may be put is as an intermediate in the preparation of heat-resistant polyester resins. For instance, the dichloride can be reacted with phthalic acid esters or certain phthalic acids themselves, such as dimethyl terephthalate, terephthalic acid, isophthalic acid, etc., to make polyester resins. An important use for the dichloride is in the preparation of flame and heat resistant polycarbonate resins by reacting the dichloride with precursor carbonating agents, such as phosgene, diphenyl carbonate, etc.

The polymeric compositions derived from the reaction of the dichloride here described have many applications. These polymeric compositions may be used to form fibers, films, or molded products. Thus, either by extrusion from melt or by depositing from solution, fibers derived from these polymeric compositions may be formed and used in the preparation of various textile materials designed for clothing and similar applications.

Various fillers may be incorporated in the polymeric compositions prior to molding thereof. Among such fillers may be mentioned glass fibers, carbon black, titanium dioxide, silica, mica, bentonite, etc. Molded products derived from such a mixture of ingredients can be used as gears, handles for cooking utensils, etc. The incorporation of abrasive particles such as carborundum, diamond powder, etc., makes molded products derived from such polymeric compositions useful as grinding wheels, etc. The addition of carbon, silicon carbide, powdered metal, conducting oxides, etc., to the polymeric compositions results in the so-called resistance or semi-conducting paints which have many useful applications.

It will of course be understood by those skilled in the art that in addition to the conditions and concentrations of ingredients described in the foregoing examples, other conditions and concentrations may be used without departing from the scope of the invention. It is intended to include within the scope of the claims herein appended any changes or modifications which may be indicated as advantageous in the practice of the invention.

What I claim as new and desire to secure by Letters Patent of the United States is:

1. In a process for dehydrohalogenating the trichloride, 1,1,1-trichloro-2,2-bis-(4-hydroxyphenyl) ethane, to form the dichloride of the formula

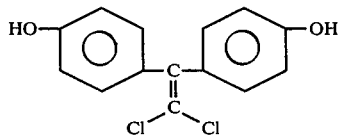

which process comprises (1) treating the aforesaid trichloride with anhydrous liquid ammonia in an amount sufficient to act as both a dehydrohalogenating agent and solvent, the improvement comprising the said liquid ammonia containing an amount of an alkyl amine effective to accelerate the dehydrohalogenation reaction, wherein said alkyl amine is selected from the class consisting of methylamine hydrochloride and bromide, ethylamine hydrochloride and bromide, and dimethylamine hydrochloride and bromide, thereby to form a substantially pure dichloroethylene compound of the above formula, and (2) removing the unreacted ammonia and alkyl amine thereby isolating the desired dichloride.

2. The process as in claim 1 wherein the alkyl amine comprises from 0.5 to 20%, by weight, based on the weight of the ammonia.

3. The process as in claim 1 wherein there is present a molar ratio of from 2 to 20 mols liquid ammonia per mol trichloride.

4. The process as in claim 1 wherein the alkyl amine is methylamine hydrochloride.

5. The process as in claim 1 wherein the alkyl amine is ethylamine hydrochloride.

6. The process as in claim 1 wherein the alkyl amine is dimethylamine hydrochloride.

7. In a process for dehydrohalogenating the trichloride, 1,1,1-trichloro-2,2-bis(4-hydroxyphenyl) ethane, to form the dichloride of the formula

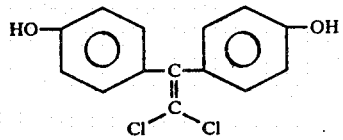

which process comprises (1) treating the aforesaid trichloroethane with anhydrous liquid ammonia in an amount sufficient to act as both dehydrohalogenating agent and solvent, the improvement comprising the said liquid ammonia containing an amount of methylamine hydrochloride effective to accelerate the dehydrohalogenation reaction, and (2) removing the unreacted ammonia and methylamine hydrochloride to yield the above-described dichloride.